United States Patent
Bergstrand et al.

[11] Patent Number: 6,153,641
[45] Date of Patent: Nov. 28, 2000

[54] PHARMACEUTICALLY ACTIVE COMPOUNDS

[75] Inventors: Håkan Bergstrand, Bjärred; Thomas Högberg, Åkarp; Kostas Karabelas; Anders Tunek, both of Lund, all of Sweden

[73] Assignee: Astra Aktiebolag, Sodertalje, Sweden

[21] Appl. No.: 08/981,003

[22] PCT Filed: Sep. 8, 1997

[86] PCT No.: PCT/SE97/01504

§ 371 Date: Dec. 18, 1997

§ 102(e) Date: Dec. 18, 1997

[87] PCT Pub. No.: WO98/11102

PCT Pub. Date: Mar. 19, 1998

[51] Int. Cl.[7] .................... A61K 31/404; A61P 37/00; C07D 403/04
[52] U.S. Cl. .................... 514/414; 546/277.4; 548/455
[58] Field of Search .................... 548/466, 468, 548/455; 514/429, 414

[56] References Cited

U.S. PATENT DOCUMENTS

| | | | |
|---|---|---|---|
| Re. 28,973 | 9/1976 | Welstead, Jr. | 260/293.61 |
| 3,642,803 | 2/1972 | Welstead, Jr. | 260/293.61 |
| 3,821,389 | 6/1974 | Grivas | 424/270 |
| 4,031,221 | 6/1977 | Helsley et al. | 424/267 |
| 4,062,869 | 12/1977 | Weston | 260/326.16 |
| 4,598,079 | 7/1986 | Beyerle et al. | 514/252 |
| 5,057,614 | 10/1991 | Davis et al. | 548/466 |
| 5,077,293 | 12/1991 | Smith et al. | 514/253 |
| 5,192,770 | 3/1993 | Clark et al. | 514/305 |
| 5,380,746 | 1/1995 | Barth et al. | 514/414 |
| 5,399,712 | 3/1995 | Hill | 578/455 |
| 5,516,915 | 5/1996 | Barth et al. | 548/455 |
| 5,543,636 | 8/1996 | Heath et al. | 514/214 |
| 5,545,636 | 8/1996 | Heath et al. | 514/214 |
| 5,621,101 | 4/1997 | Lewis et al. | 540/545 |
| 5,705,511 | 1/1998 | Hudkins et al. | 514/338 |

FOREIGN PATENT DOCUMENTS

| | | |
|---|---|---|
| 0 464 604 A2 | 1/1992 | European Pat. Off. . |
| 0 490 263 A1 | 6/1992 | European Pat. Off. . |
| 0 540 956 A1 | 11/1993 | European Pat. Off. . |
| 0 675 125 A1 | 10/1995 | European Pat. Off. . |
| 76311450 | 3/1973 | France . |
| 1 500 176 | 2/1978 | United Kingdom . |
| WO 93/18765 | 9/1993 | WIPO . |
| WO 95/17182 | 6/1995 | WIPO . |
| WO 96/01825 | 1/1996 | WIPO . |
| WO 98/13368 | 4/1998 | WIPO . |
| WO 98/43632 | 10/1998 | WIPO ................. A61K 31/235 |

OTHER PUBLICATIONS

Bergstrand et al., "Modulation of Neutrophil Superoxide Generation by Inhibitors of Protein Kinase C, Calmodulin, . . . ", The Journal of Pharmacology and Experimental Therapeutics, 1992, 263(3):1334–1346.

Chakravarthy et al., "The Direct Measurement of Protein Kinase C (PKC) Activity in Isolated Membranes Using a Selective Peptide Substrate", Analytical Biochemistry, 1991, 196:144–150.

Granet et al., "A Microtiter Plate Assay for Protein Kinase $C^1$", Analytical Biochemistry, 1987, 163:458–463.

Olsson et al., Activation of Human Neutrophil Protein Kinase C in vitro by 1,2–isopropylidene–3–decanoyl–sn–glycerol (Ip($COC_9$), Cellular Signaling, 1989, 1(4):405–410.

Gazit et al., "Tyrphostins. 5. Potent Inhibitors of Platelet–Derived Growth Factor Receptor Tyrosine Kinase: Structure–Activity Relationships . . . ", J. Med. Chem., 1996, vol. 39, pp. 2170–2177.

U.S.S.N. 08/973,652, filed Dec. 1997.
U.S.S.N. 08/981,212, filed Aug. 1, 1997.
U.S.S.N. 08/981,266, filed Dec. 1997.

Glazunov et al., "Riboflavine operon in *Bacillus subtilis* . . . ", Chemical Abstracts, 1975, vol. 82, No. 82817b.

*Primary Examiner*—Robert W. Ramsuer
*Attorney, Agent, or Firm*—Fish & Richardson P.C.

[57] ABSTRACT

The present invention provides novel compounds of the formula (I):

$$R_{20}-(CH_2)_n-R \qquad (I)$$

wherein:

$T_{20}$ is a bisindolylmaleimide moiety linked to the $-(CH_2)_n$-group through an indolyl nitrogen, n is 0 or 1, R is a 5 or 6 membered aromatic carbocyclic or heterocyclic ring, the heterocyclic ring containing N or S, R is substituted by $R_1$ and up to four of $R_2$, $R_3$, $R_4$ and $R_5$, wherein;

$R_1$ is aminomethyl, (N—($C_{1-4}$-alkyl)amino)methyl, (N,N-di($C_{1-4}$-alkyl)amino)methyl or pyridiniummethyl, and $R_2$, $R_3$, and $R_4$ and $R_5$ (if present), which may be the same or different, are each hydrogen, hydroxy, $C_{1-4}$-alkoxy, $C_{1-4}$-alkoxy) or halogen, or $R_2$ when in a position contiguous to the bond connecting R to the $-(CH_2)_n-$ group and n is 1 may, together with the 2-carbon atom on the indole to which the $-(CH_2)$ group is attached, form a ring, and pharmaceutically acceptable salts thereof; and the use of such compounds in medical therapy.

27 Claims, No Drawings

PHARMACEUTICALLY ACTIVE COMPOUNDS

This is a continuation of International Patent Application No. PCT/SE97/01504, with an international filing date of Sep. 08, 1997, now pending.

FIELD OF THE INVENTION

The present invention relates to novel bisindolylmaleimides, methods for their preparation and use, intermediates therefore and pharmaceutical compositions comprising them.

BACKGROUND AND PRIOR ART

Protein kinase C (PKC) is a family of phosplolipid-dependent serine/threonine-specific protein kinases which play an important role in cellular growth control, regulation and differentiation.

Since the activation of PKC has been implicated in several human disease processes, including various forms of cancer, different forms of inflammatory and/or immunological disorders as well as some neurological disorders, inhibition of PKC could be therapeutic value in treating these conditions.

Several classes of compounds have been identified as PKC inhibitors, e.g., isoquinoline sulfonamides, sphingosine and related sphingolipids and indolocarbazoles.

EP, B1, 0328026 discloses the use of certain bisindolylmaleimides, a class of compounds related to the indolocarbazoles, in medicaments for the treatment of various diseases.

Little work has been done on the design of PKC inhibitors with a favorable topical/systemic effect ratio. In fact, PKC is an ubiquitous enzyme with wide-ranging physiological functions, and the use of non-specific PKC inhibitors would be expected to be accompanied by severe systemic side effects.

OUTLINE OF THE INVENTION

We have found a group of novel bisindolylmaleimides which, relative to known PKC inhibitors, have improved ability to inhibit PKC and/or are more quickly metabolised to less active compounds. The compounds of formula (I) and pharmaceutically acceptable salts thereof are active topically, and have the potential to become deactivated systemically as indicated by Example 23 hereinafter. Compounds of the present invention are preferably administered via inhalation therefore a rapid lung metabolism is highly desirable in order that the compound may exert its therapeutic effect at the target site and then be rapidly degraded to a relatively inactive metabolite.

The object of the present invention is to provide these novel bisindolylmaleimides, methods for their preparation and intermediates used for their preparation.

Another object of the present invention is the use of the novel compounds for the treatment of inflammatory and immunological disorders and preferably of the topical treatment of inflammatory and immunological disorders, such as the topical treatment of airway diseases involving inflammatory conditions, e.g. asthma; bronchitis and atopic diseases, e.g. rhinitis and atopic dermatitis; psoriasis; inflammatory bowel diseases, e.g. Chrohn's disease and colitis; rheumatoid arthritis and malignant diseases (e.g. skin and lung cancer).

Still another object of the invention is a pharmaceutical composition comprising a compound according to the invention, as active ingredient, together with a pharmaceutically acceptable adjuvant, diluent or carrier.

DETAILED DESCRIPTION OF THE INVENTION

According to the present invention we provide novel compounds of formula (I)

$$R_{20}-(CH_2)_n-R \qquad (I)$$

wherein:
$R_{20}$ is a bisindolylmaleimide moiety linked to the $-(CH_{2[<m]ditl})_n$-group thorough an indolyl nitrogen,
n is 0 or 1,
R is a 5 or 6 membered aromatic carbocyclic or heterocyclic ring, the heterocyclic ring containing N or S,
R is substituted by $R_1$ and up to four of $R_2$, $R_3$, $R_4$ and $R_5$, wherein:
R is aminomethyl, (N—($C_{1-4}$-alkyl)amino)methyl, (N,N-di($C_{1-4}$-alkyl)amino)methyl or pyridiniummethyl, and
$R_2$, $R_3$, and $R_4$ and $R_5$ (if present) which may be the same or different, are each hydrogen, hydroxy, $C_{1-4}$-alkoxy, $C_{1-4}$-alkyl, tri($C_{1-4}$-alkyl)silyl($C_{1-4}$-alkoxy) or halogen, or $R_2$ when in a position contiguous to the bond connecting R to the —$(CH_2)_n$— group and n is 1 may, together with the 2-carbon atom on the indole to which the —$(CH_2)$ group is attached, form a ring,
and pharmaceutically acceptable salts thereof.

Preferred compounds of formula (I) are compounds of formula (IA):

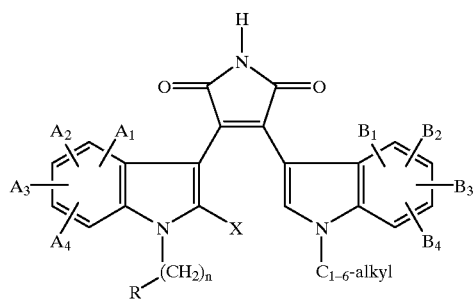

(IA)

wherein:
$A_1, A_2, A_3, A_4, B_1, B_2, B_3,$ and $B_4$, which may be the same or different, are each hydrogen, $C_1-C_4$ alkyl, $C_1-C_4$ alkoxy, carboxy $C_1-C_4$ alkyl or halogen;
n, R, R1, R3, R4, and R5 are as defined above, and
$R_2$ is as defined above, except that when in a position contiguous to the bond connecting R to the —$(CH_2)_n$-group and n is 1, may together with X form a bond, or
X may be hydrogen; and
pharmaceutically acceptable salts thereof.

Particularly preferred compounds of the present invention include:
3-[1-(3-Aminomethylbenxyl)-indol-3-yl]-4-(1-methyl-indol-3-yl)-pyrrole-2,5-dione,
3-[1-(4-Aminomethylbenzyl)-indol-3-yl]-4-(1-methyl-indol-3-yl)-pyrrole-2,5-dione,
3-[1-(5-Aminomethyl-2-bromobenzyl)-indol-3-yl]-4-(1-methyl-indol-3-yl-pyrrole-2,5-dione,
3-[1-(3-Aminomethylbenzyl)-5-methoxy-indol-3-yl]-4-(1-methyl-5-methoxy-indol-3-yl)-pyrrole-2,5-dione, 3-[1-(3-Aminomethylbenzyl)-7-ethyl-indol-3-yl]-4-(1-methyl-indol3-yl)-pyrrole-2,5-dione, 3-[1-(6-Aminomethyl-pyridin-2-ylmethyl)-indol-3-yl]-4-(1-methyl-indol-3-yl)-pyrrole-2,5-dione, 3-[1-(5-Aminomethyl-thiopen-2-ylmethyl)-indol-3-yl]-4-(1-methyl-indol-3-y)-pyrrole-2,5-dione, 3-[1-(3-Aminomethylbenzyl)-5-carboxymethyl-indol-3-yl]-4-(1-methyl-indol-3-yl)-pyrrole-2,5-dione, and more preferably:

3-[1-(3-Aminomethylbenzyl)-indol-3-yl]-4-(1-methyl-indol-3-yl)-pyrrole-2,5-dione, 3-[1-(3-Aminomethylbenzyl)-5-methoxy-indol-3-yl]-4-(1-methyl-5-methoxy-indol-3-yl)-pyrrole-2,5-dione, 3-[-1-(6-Aminomethyl-pyridin-2-ylmethyl)-indol-3-yl]-4-(1-methyl-indol-3-yl)-pyrrole-2,5-dione, 3-[1-(5-Aminomethyl-thiopen-2-ylmethyl)-3-yl]-4-(1-methyl-indol-3-yl)-pyrrole-2,5-dione, 3-[1-(3-Aminomethylbenzyl)-5-carboxymethyl-indol-3-yl]-4-(1-methyl-indol-3-yl)-pyrrole-2,5-dione, and most preferably 3-[1-(3-Aminomethylbenzyl)-indol-3-yl]-4-(1-methyl-indol-3-yl)-pyrrole-2,5-dione, and pharmaceutically acceptable salts thereof, particularly the hydrochloride salts thereof.

METHODS OF PREPARATION

The compounds of formula (IA) and pharmaceutically acceptable salts thereof may be prepared by a) production of a compound of formula (I) in which $R_1$ is aminomethyl, by reduction of a corresponding compound in which $R_1$ is azidomethyl, or b) reaction of
  (i) a compound of formula (III)

$HNR_7R_8$  (III)

in which $R_7$ and $R_8$, which may be the same or different, are each hydrogen or $C_{1-4}$-alkyl, or
  (ii) pyridine with a corresponding compound of formula (I) in which $R_1$ is a methyl group carrying a good leaving group, or c) production of a compound of formula (I) in which $R_1$ is a aminomethyl, by reaction of a compound of formula (I) in which $R_1$ is a methyl group carrying a protected amino group, with a deprotecting agent, or d) production of a compound of formula (I) in which $R_1$ is aminomethyl by reaction of a compound of formula (IV)

(IV)

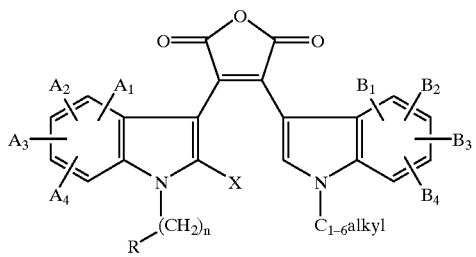

in which $A_1-A_4$, $B_1-B_4$, n and R are defined as in formula (I), but in which $R_1$ is a methyl group carrying a protected amino group, with (i) ammonia followed by treatment with a deprotecting agent; or (ii) ammonium acetate followed by treatment with a deprotecting agent; or (iii) hexamethyldisilazane followed by treatment with a deprotecting agent; or e) production of a compound of formula (I) in which $R_1$ is aminomethyl, by reaction of ammonia with a compound of formula (IV) in which $A_1-A_4$, $B_1-B_4$, X, n and R are defined as in formula (I), but in which $R_1$ is a methyl group carrying a halogen, or f) production of a compound of formula (I) in which $R_1$ is a (N—($C_{1-4}$-alkyl)amino)methyl or (n,N-di($C_{1-4}$-alkyl)amino)methyl, by reaction of ammonia with a compound of formula (IV) in which $A_1-A_4$, $B_1-B_4$, X, n and R are defined as in formula (I), but in which $R_1$ is (N—($C_{1-4}$-alkyl)amino)methyl or (n,N-di($C_{1-4}$-alkyl)amino)methyl, or g) production of a compound of formula (I) in which one or more or $R_2$, $R_3$, and $R_4$ and $R_5$ (if present), are hydroxyl, by reaction of a compound of formula (I) in which one or more or $R_2$, $R_3$, and $R_4$ and $R_5$ (if present), are oxygen carrying a protecting group, with a deprotecting agent, or h) converting a compound of formula (I) to a pharmaceutically acceptable salt thereof, of vice versa.

In process a) the conditions for the reduction are well known to those skilled in the art. Preferred conditions are:

i) hydrogenation over Pd/C or Lindlar catalyst, e.g. at atmospheric pressure and at a temperature of 10–30° C. and using a protic solvent, e.g. ethanol or a mixture of ethanol and ethyl acetate;

ii) triphenyl phosphine in a suitable solvent, e.g. tetrahydrofuran at a temperature of 10–30° C., e.g. for about 30 min followed by treatment with 1 M sodium hydroxide or ammonium hydroxide (25% by volume) at a temperature of 10–30° C. overnight.

In process b) the hydroxyl group $R_1$ which is hydroxymethyl may be transformed to a better leaving group, e.g. methyanesulfonyloxy group, and subsequently treated with an amine such as ammonia, methylamine or dimethylamine. Suitable leaving groups are well known to those skilled in the art. A preferred leaving group is mesylate. The intermediate compound possessing a good leaving group may be isolated or generated in situ.

In process c) the protected amino group may be a phthaloyl, a trifluoroacetamide or a t-butyloxycarbonyl amino group. The phthaloyl group may be deprotected by treatment with an excess of an amine, e.g. methylamine (e.g. 7.6 M in ethanol) in a polar solvent, e.g. tetrahydrofuran at a temperature of 10–30° C. overnight. Deprotection of the trifluoroacetamide may be performed using excess ammonia e.g. in acetone at a temperature of 10–30° C. overnight. The t-butyloxycarbonyl group may be removed using excess hydrochloric acid (e.g. 5M) in a polar solvent, e.g. tetrahydrofuran at about 30–60° C. for about 30 min.

In process d) the protected amino group may be a phthaloyl group, and preferred conditions for the reaction are:

i) reaction with ammonia, e.g. at elevated temperature;

ii) reaction with ammonium acetate, e.g. at elevated temperature followed by treatment with an amine, e.g. methylamine; or iii) reaction with hexamethyldisilazane in a polar solvent, e.g. methanol at a temperature of 10–30° C. followed by treatment with an amine, e.g. methylamine.

In process e) the halogen is preferably bromine or chlorine, and the reaction with ammonia (e.g. ammonium hydroxide) may be carried out in a polar solvent, e.g. dimehtylformamide, e.g. at elevated temperature.

In process f) the reaction with ammonia (e.g. aqueous ammonia) is carried out e.g. at elevated temperature.

In process g) the protecting group may be a tri($C_{1-4}$-alkyl)silyl($C_{1-4}$-alkoxy)($C_{1-4}$-alkyl) e.g. (trimethylsilyl)ethoxymethyl. The deprotecting agent may be for example trifluoroacetic acid, and the deprotecting step may be carried out in a suitable solvent, e.g. methylene chloride.

In process h) the conversion may be carried out by conventional processes known per se, e.g. reaction of the free base with an acid containing the desired anion, or by careful basicfication of the salt. The reaction may be carried out in a suitable solvent, e.g. ethanol or methylene chloride.

The starting materials for the above processes may be made by the methods set out in the Examples or by methods analogous thereto. Other conventional methods for making the starting materials will be evident to those skilled in the art.

Compounds of formula (I) which are not of formula (IA) may be made by methods analogous to the methods disclosed herein for the syntheses of compounds of formula (IA).

Within the methods set out in the Examples the following general intermediates, which also are an object of the invention, are disclosed:

i) A compound of formula (IB) defined as in formula (IA) above but in which $R_1$ is azidomethyl, hydroxymethyl, a methyl group carrying a good leaving group, or a methyl group carrying out a protected amino group, preferably a phthaloyl, a trifluoroacetamide or a t-butyloxycarbonyl amino group.

ii) A compound of formula (IV) above which $R_1$ is a methyl group carrying either a protected amino group, preferably a phthaloyl, a trifluoroacetamide or a t-butyloxycarbonyl amino group, or a halogen, preferably bromine or chlorine, or $R_1$ is a (N—($C_{1-4}$-alkyl)amino)methyl or (N,N-di($C_{1-4}$-alkyl)amino)methyl.

iii) A compound of formula (V)

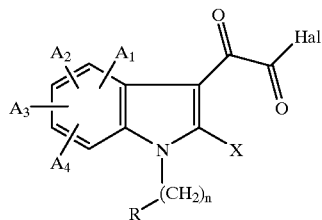

(V)

wherein $A_1, A_2, A_3, A_4$, X, n and R are defined as in formula (IA) above, and in which $R_1$ is a methyl group carrying a protected amino group, preferably a phthaloyl, a trifluoroacetamide or a t-butyloxycarbonyl amino group, and Hal is an halogen atom, preferably chlorine.

iv) A compound of formula (VI)

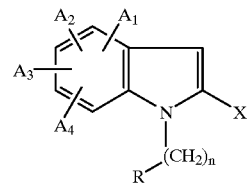

(VI)

wherein:

$A_1, A_2, A_3, A_4$, X, n and R are defined as in formula (IA) above, and in which $R_1$ is a methyl group carrying a protected amino group, preferably a phthaloyl, a trifluoroacetamide or t-butyloxycarbonyl amino group.

The compounds of formula (I) and pharmaceutically acceptable salts thereof are useful because they demonstrate pharmacological activity. In particular they demonstrate activity as PKC inhibitors, e.g. as shown by their activity in the in vitro assays described in Granet, R. A. et al, Analyt. Biochem. 1987; 163, 458–463; Olsson, H. et al, Cell Signal 1989, 1, 405–410; and Chakravarthy, B. R. et al, Analyt. Biochem. 1991, 196, 144–150. The compounds are generally active in the above test with $IC_{50}$-values ranging from 10–1000 nM.

The compounds of formula (I) and pharmaceutically acceptable salts thereof are active topically, and also have the potential to become deactivated systemically.

The compounds of formula (I) and pharmaceutically acceptable salts thereof are indicated for use in the treatment (and preferably the topical treatment) of inflammatory and immunological disorders, e.g. the topical treatment of airway diseases involving inflammatory conditions, e.g. asthma; bronchitis and atopic diseases, e.g. rhinitis and atopic dermatitis; psoriasis; inflammatory bowel diseases, e.g. Chron's disease and colitis; rheumatoid arthritis and malignant diseases, (e.g. skin and lung cancer). For the treatment of the above conditions the compounds may be administered at a dosage from 10 µg to 10 mg per day either as a single dose or in divided doses 2to 4 times per day. Thus unit doses comprise from 2.5 µg to 10 mg of a compound according to the invention. The compounds may be administered topically, e.g. to the lung and/or airways, in the form of solutions, suspensions, HFA aerosols and dry powder formulations, e.g. Turbuhaler® formulations.

According to the invention the compounds of formula (I), and pharmaceutically acceptable salts thereof, may be administered on their own or as a pharmaceutical composition comprising the compound of formula (I), or the pharmaceutically acceptable salt thereof, in combination with a pharmaceutically acceptable diluent, adjuvant or carrier. Particularly preferred are compositions not containing material capable of causing an adverse, e.g. allergic, reaction.

Dry powder formulations and pressurized HFA aerosols of the compound of formula (I), or the pharmaceutically acceptable salts thereof, may be administered by oral or nasal inhalation. For inhalation the compound is desireably finely divided. The finely divided compound preferably has a mass median diameter of less than 10 µm, and may be suspended in a propellant mixture with the assistance of a dispersant, such as a $C_8$–$C_{20}$ fatty acid or salt thereof, (e.g. oleic acid), a bile salt, a phospholipid, an alkyl saccharide, a perfluorinated or polyethyoxylated surfactant, or other pharmaceutically acceptable dispersant.

The compound may also be administered by means of a dry powder inhaler. The inhaler may be a single dose inhaler, or it may be a multi dose inhaler, e.g. a multi dose, breath actuated, dry powder inhaler, or a unit dose breath actuated, dry powder inhaler.

One possibility is to mix the finely divided compound with a carrier substance, e.g. a mono-, di- or polysaccharide, a sugar alcohol or other polyols. Suitable carriers are sugars such as lactose, glucose, raffinose, metlzitose, lactitol, maltitol, trehalose, sucrose, mannitol; and starch. Alternatively the finely divided compound may be coated by another substance. The powder mixture may also be dispensed into hard gelatin capsules, each containing the desired dose of the active compound.

When the powder preparation of the present invention is intended for oral or nasal inhalation as dry powder or an aerosol, the compounds of formula (I), or pharmaceutically acceptable salts thereof, should preferably consist of (a) primary particles having a diameter of less than about 10 microns and preferably less than 5 microns, or (b) weak agglomerates of said particles.

The carrier in the powder preparation for oral or nasal inhalation may largely consist of particles having a diameter of less than about 01 microns so that the resultant powder as a whole consists of optionally agglomerated primary particles having a diameter of less than about 01 microns; alternatively the carrier may largely consist of much bigger particles ("coarse particles"), so that an "ordered mixture" may be formed between the active compound and the carrier. In the ordered mixture, alternatively known as an interactive or adhesive mixture, the fine particles of the active agent will be fairly evenly distributed over the surface of the coarse carrier. Preferably in such a case the active compound is not in the form of agglomerates prior to formation of the ordered mixture. The coarse particles may have a diameter of over 20 microns, e.g. over 60 microns. Above these lower limits, the diameter of the coarse particles is not of critical importance so various coarse particle sizes may be used, if desired according to the practical requirements of the particular formulation. There is no requirement for the coarse particles in the ordered mixture to all be of the same size, but the coarse particles may all advantageously be of similar size within the ordered mixture. Preferably, the coarse particles have a diameter of 30—800, and preferably 30—130, microns.

Another possibility is to process the finely divided powder in to spheres which break up during the inhalation procedure. This spheronized powder may be filled into the drug reservoir of a multidose inhaler, e.g. that known as the Turbuhaler® in which a dosing unit meters the desired dose which is then inhaled by the patient. With this system the active compound, with or without a carrier substance, is delivered to the patient.

The compounds of the invention may also be administered in conjunction with other compounds used for the treatment of the above conditions.

For compounds of formula (IA), the following independent preferences apply:

$A_1$, $A_2$, $B_1$ and $B_2$ are hydrogen, $A_3$, $A_4$, $B_3$ and $B_4$, which may be the same or different, are each hydrogen, $C_1$–$C_3$ alkyl, $C_1$–$C_3$ alkoxy, carboxy $C_1$–$C_3$ alkyl, or halogen;

n is 0 or 1;

$R_1$ is aminomethyl, (N—($C_{1-4}$-alkyl)amino)methyl or (N,N-di($C_{1-4}$-alkyl)amino)methyl, or $R_2$, $R_3$, and $R_4$ and $R_5$ (if present), which may be the same or different, are each hydrogen, hydroxy, $C_1$–$C_3$ alkyl, $C_1$–$C_6$ alkoxy or halogen, or $R_2$, when in a position contiguous to the bond connecting R to the —$(CH_2)_n$-group and n is 1, may together with X form a bond; or X may be hydrogen;

more particularly:

$A_1$, $A_2$, $A_3$, $B_1$, $B_2$, and $B_3$ are hydrogen, $A_4$ and $B_4$, which may be the same or different, are each hydrogen, ethyl, methoxy, carboxymethyl, or halogen, n is 1, $R_1$ is aminomethyl, or $R_2$, $R_3$, and $R_4$ and $R_5$ (if present), which may be the same or different, are each hydrogen, hydroxy, methoxy, methyl or halogen, or $R_2$, when in a position contiguous to the bond connecting R to the —$(CH_2)_n$-group, may together with X form a bond, or X may be hydrogen;

and yet more particularly:

$R_1$ is aminomethyl, $R_1$ is in a position para or meta (more preferably meta) to the —$(CH_2)_n$-group, R is phenyl, pyridyl or thiopheynl (more preferably phenyl), and when R is thiophenyl the —$(CH_2)_n$-group is in the 2-position and the $R_1$ group is in the 5-position of the thiophene ring.

$R_2$ to $R_5$ are all hydrogen or one of $R_2$ to $R_5$ may be bromo, $A_1$, $A_2$, $A_3$, $B_1$, $B_2$, and $B_3$ are hydrogen, and/or $A_4$ and $B_4$, which may be the same or different, are each hydrogen, methoxy, or carboxymethyl, and pharmaceutically acceptable (preferably acid addition) salts thereof.

Pharmaceutically acceptable salts of the compound of the formula (I) and formula (IA) include the hydrochlorides, hydrobromides, acetates, benzoates and sulphonates, preferably the hydrochloride.

The following Examples illustrate, but in no way limit the invention.

All reactions were performed in dried glassware under Ar or $N_2$ unless otherwise noted. Tetrahydrofuran was distilled from sodium/benzophenone. Dimethyl formamide and dichloromethane were distilled form calcium hydride, or dried over molecular sieves. The ammonium hydroxide used had a concentration of 25% v/v, unless otherwise states, and all commercial reagents were used as received.

Chromatography was carried out using a Chromatotron® (a centrifugally accelerated, radial preparative thin-layer chromatograph), the plates used were prepared using Merck Silica Gel $PF_{254}$ containing gypsum.

$^1$H-NMR spectra were recorded on a Varian XL-300 Unity-500+instrument. The central solvent peaks of chloroform-d ($\delta_H$ 7.24 ppm), methanol-$d_4$ ($\delta_h$ 3.34 ppm), dimethyl sulphoxide-$d_6$ ($\delta_H$ 2.50 ppm) and acetone-$d_6$ ($\delta_H$ 2.05 ppm) were used as internal references. Low-resolution mass spectra and accurate mass determinations were recorded on an Autospec-Q, Fisons Analytical, double focusing sector instrument equiped with a LSIMS interface.

EXAMPLE 1

3-[1-(3-Aminomethylbenzyl)-indol-3-yl]-4-(1-methyl-indol-3-yl)-pyrrole-2,5-dione hydrochloride a) 3-[1-(3-Hydroxymethyl-benzyl)-indol-3-yl]-4-(1-methyl-indol-3-yl)-pyrrole-2,5-dione A solution of 3-indol-3-yl)-4-(1-methyl-indol-3-yl)-furan-2,5-dione (2.0 g, 5.85 mmol) and NaH (0.2 g, 8 mmol) in dry dimethylforamide (30 ml) was stirred for 20 min at room temperature. Acetic acid 3-bromomethyl benzylester (1.415 g, 5.82 mmol) was added in one portion and the solution was stirred for 16 h. The mixture was then poured into an excess of 2 M HCl (aq) and extracted with ethyl acetate. The organic phase was washed with water and dried ($Na_2SO_4$). Filtration and evaporation afforded 2.9 g of the crude 3-[1-(3-acetoxymethyl-benzyl)-indol-3-yl]-4-(1-methyl-indol-3-yl)-furan-2,5-dione.

A portion (400 mg) of the crude compound was dissolved in dimethylformamide (20 mL) and ammonium hydroxide (20 mL) and heated in a sealed tube at 140° C. for 2 h. After an additional 16 h at room temperature, the mixture was poured into ethyl acetate and water, the organic phase separated, washed with water and dried ($Na_2SO_4$). Chromatography (ethyl acetate/heptane:2:1) gave the sub-title product (0.299 g) as a red powder.

$^1$H-NMR ($CDCl_3$):δ7.74 (1H, s);7.67 (1H,s); 7.66 (1H, s); 732–7.14 (5H, m); 712–6.98 (4H, m); 6.83 (1H, d, J=8.3 Hz); 6.75 (1H, t, J=7.8 Hz); 6.68 (1H, t, J=7.8 Hz); 5.31 (2H, s); 4.64 (2H, d, J=5.9 Hz); 3.84 (3H, s).

b) 3-[1-(3-Methanesulfonyloxymethylbenzyl)-indol-3-yl]-4-(1-methyl-indol-3-yl)-pyrrole-2,5-dione Methanesulfonic anhydride (0.35 g, 2.0 mmol) was added to a stirred solution of the product of step a) (0.234 g, 0.51 mmol) and 2,6-di-tert-butyl-4-methylpyridine (0.42 g, 2.0 mmol) in dry $CH_2Cl_2$ (15 mL) at room temperature. The reaction mixture was stirred for 16 h, and thereafter quenched by adding methanol (1.5 mL). The solvent was evaporated and the crude product chromatographed (ethyl acetate/heptane: 2/1) to yield 0.285 g of the sub-title product.

$^1$H-NMR ($CDCl_3$):δ7.76 (1H, s); 7.66 (1H, s); 7.58 (1H, s); 7.38–7.24 (3H, m); 7.22–7.00 (6H, m); 6.82 (1H, d, J=8.05 Hz); 6.77 (1H, t, J=8.30 Hz); 6.68 (1H, t, J=8.05 Hz); 5.34 (2H, s); 5.18 (2H, s); 3.86 (3H, s); 2.83 (3H, s).

c) 3-[1-(3-Azidomethylbenzyl)-indol-3-yl]-4-(1-methyl-indol-3-yl)-pyrrole-2,5-dione Sodium azide (0.144 g, 2.2 mmol) was added to a solution of the product of step b) (0.28 g, 0.5 mmol) in dry dimethylformamide (5 mL). The mixture was stirred at room temperature for 30 min and then partitioned between ethyl acetate and water. The organic phase was washed three times with water and evaporated (with ethanol), to give the crude sub-title product which was used without further purification.

d) A dispersion of Lindlar catalyst (0.150 g) in ethanol (10 ml) was hydrogenated at atmospheric pressure for 15 min. Then, a solution of the product of step c) (0.187 g, 0.38 mmol) in ethyl acetate (3 mL) was added with a syringe, and the resulting mixture stirred vigorously for 45 h. The solution was filtered through Celite® (a silica gel) and the solvents evaporated. Chromatography on silica (ethyl acetate/methanol/ammonium hydroxide; 80/20/2; v/v) furnished 20.1 mg of 3-[1-(3-aminomethylbenzyl)-indol-3-yl]-4-(1-methyl-indol-3-yl)-pyrrole-2,5-dione which was dissolved in ethanolic HCl (1.5 M), evaporated, dissolved in methanol, evaporated to dryness, dissolved in water and freeze dried to afford the title compound.

$^1$H-NMR ($CD_3OD$):δ7.79 (1H, s); 7.78 (1H, s);7.46–7.40 (2H, m); 7.40–7.35 (2H, m); 7.32 (1H, d, J=8.4 Hz); 7.25 (1H, d, J=7.1 Hz); 7.08 (1H, t, J=7.7 Hz); 7.02 (1H, t, J=7.7 Hz); 6.97 (1H, d, J=7.9 Hz); 6.80 (1H, d, J=7.9 Hz); 6.69 (1H, t, J=7.7 Hz); 6.62 (1H, t, J=7.5 Hz); 5.48 (2 H, s); 4.10 (2H, s); 3.89 (3H, s).

EXAMPLE 2

3-[1-(4-Aminomethylbenzyl)-indol-3-yl]-4-(1-methyl-indol-3-yl)-pyrrole-2,5-dione This compound was prepared using a process analogous to that used in Example 1.

$^1$H-NMR (acetone-d6):δ3.94 (3H, s), 4.42 (2H, s), 5.51 (2H, s), 6.65 (1H, dt, J7.7, 1.1 Hz), 6.69 (1H, dt, J7.7, 1.1 Hz), 6.86 (1H, d 8.0 Hz), 6.97–7.10 (3H, m), 7.16–7.22 (2H, m), 7.31–7.42 (4H, m), 7.84 (1H, s), 7.85 (1H, s).

MS-FAB:m/z 461 [MH$^+$].

EXAMPLE 3

3-[1-(3-Aminomethyl-2,6-dimethoxybenzyl)-indol-3-yl]-4-(1-methyl-indol-3-yl)-pyrrole-2,5-dione a) 3-[1-(3-Hydroxymethyl-2,6-dimethoxybenzyl)-indol-3-yl]-4-(1-methyl-indol-3-yl)-pyrrole-2,5-dione was prepared in a manner analogous to Example 1 a). Thus, the anion of 3-(indol-3-yl)-4-(1-methyl-indol-3-yl)-furan-2,5-dione was treated with acetic acid 3-bromomethyl-2,4-dimethoxy-benzyl ester. Subsequent treatment with ammonia gave the desired alcohol.

$^1$H-NMR (dimethylformamide-d$_7$):δ7.92 (1H, s); 7.90 (1H, s); 7.74 (1H, d, J=8.3 Hz); 7.55 (1H, d, J=8.6 Hz); 7.50 (1H, d, J=8.2 Hz); 7.09 (2H, t, J=7.0 Hz); 6.98 (1H, d, J=8.6 Hz); 6.92 (1H, d, J=4.2 Hz); 6.90 (1H, d, J=4.2 Hz); 6.65 (2H); 5.50 (2H, s); 5.17 (1H, t, J=5.0 Hz); 4.70 (2H, d, J=5.0 Hz); 3.98 (3H, s); 3.92 (3H, s); 3.81 (3H, s).

HRMS:calcd. for $C_{31}H_{27}N_3O_5$ (M$^+$):521.1951, found: 521.1957.

b) An excess of methanesulfonic anhydride was added to a solution of the product of step a) (130 mg, 0.26 mmol) and 2,6-lutidine (980 mg, 9 mmol) in dry methylene chloride (20 mL). The mixture was stirred for 1 h at ambient temperature, and a solution of 5% ammonia in isopropyl alcohol (6 mL) was added in one portion. After stirring for an additional hour, the mixture was evaporated and chromatographed (ethyl acetate/methanol/ammonium hydroxide:80/20/2 v/v) to give 17 mg of the title compound. This was impure according to NMR and therefore chromatographed once more as above, giving 5.5 mg of the pure product.

$^1$H-NMR ($CDCl_3$):δ7.78 (1H, s); 7.65 (1H, s); 7.56 (1H, d, J=8.5 Hz); 7.26 (1H, d, J=8.0 Hz); 7.24 (1H, d, J=7.5 Hz); 7.05 (1H, t, J=7.5 Hz); 7.04 (1H, t, J=7.5 Hz); 6.84 (1H, d, J=8.0 Hz); 6.83 (1H, d, J=8.0 Hz); 6.68 (1H, d, J=8.5 Hz); 6.67 (1H, t, J=7.5 Hz); 6.58 (1H, t, J=7.5 Hz); 5.34 (2H, s); 3.85 (2H, s); 3.82 (3H, s); 3.78 (3H, s); 3.65 (3H, s).

HRMS:calcd. for $C_{31}H_{28}N_4O_4$ (M$^+$):520.211, found:520.214.

EXAMPLE 4

3-[1-(5-Aminomethyl-2-methoxybenzyl)-indol-3-yl]-4-(1-methyl-indol-3-yl)-pyrrole-2,5-dione hydrochloride a) 3-[1-(5-Hydroxymethyl-2-methoxybenzyl)-indol-3yl]-4-(1-methyl-indol-3-yl)-pyrrole-2,5-dione This compound was prepared in a manner analogous to Example 1 a). Thus, the anion of 3-(indol-3-yl)-4-(1-methyl-indol-3-yl)-furan-2,5-dione was treated with acetic acid 3-bromomethyl-4-methoxybenzyl ester. Subsequent treatment with ammonia gave the desired alcohol.

$^1$H-NMR ($CDCl_3$):δ7.73 (1H, s); 7.68 (1H, s); 7.32–7.25 (3H, m); 7.00–7.15 (2H, m); 6.94 (1H, d, J=8.0 Hz); 6.92–6.87 (3H, m); 6.73–6.65 (2H, m); 5.34 (2H, s); 4.47 (2H, s); 3.86 (3H, s); 3.84 (3H, s)

HRMS:calcd. for $C_{30}H_{25}N_3O_4$ (M$^+$):491.1854, found: 491.1854.

b) 3-[1-(5-Azidomethyl-2-methoxybensyl)-indol-3-yl]-4-(1-methyl-indol-3-yl)-pyrrole-2,5-dione A portion of diethyl azodicarboxylate (0.1 mL, 0.5 mmol) was added dropwise to an ice-cold stirred solution of the product of step a) (190 mg, 0.39 mmol), triphenyl phosphen (153.1 mg, 0.58 mmol), and hydrazoic acid (0.6 mL, 2.6 M in toluene, 1.6 mmol) in dry tetrahydrofuran (7 mL). The resulting mixture was kept for 30 min, and then stirred at ambient temperature for 65 h. Additional triphenyl phosphine (99 mg, 0.38 mmol), hydrazoic acid (1.6 mmol as above), and diethyl azodicarboxylate (0.06, 0.3 mmol) were added and stirring was continued for another hour. The remaining hydrazoic acid was quenched by adding methanol (6 mL). Evaporation gave the crude sub-title product.

c) The crude product from step b) was subjected to a Staudinger reaction by mixing with triphenyl phosphine (214 mg, 0.82 mmol) in tetrahydrofuran (6 mL) and stirring at room temperature for 30 min. Ammonium hydroxide (1 mL) was added and the reaction was stirred overnight. Evaporation followed by chromatography (ethyl acetate/methanol/ammonium hydroxide:80/20/2) gave the title compound as the free amine. The hydrochloride was obtained by dissolving the amine in 3.4 M HCl (aq). Evaporation followed by redissolving in methanol and evaporation again afforded 51.3 mg of the title compound.

$^1$H-NMR (CD$_3$OD):δ7.82 (1H, s); 7.78 (1H, s); 7.43 (1H, d, J=8.5 Hz); 7.41 (1H, d, J=6.5 Hz); 7.38 (1H, d, J=6.5 Hz); 7.15 (1H, s); 7.13 (1H, d, J=8.5 Hz); 7.07 (1H, t, J=7.5 Hz); 7.03 (1H, t, J=8.0 Hz); 6.90 (1H, d, J=8.0 Hz); 6.81 (1H, d, J=8.0 Hz); 6.67 (1H, t, J=7.5 Hz); 6.59 (1H, t, J=8.0 Hz); 5.46 (2H, s); 3.99 (2H, s); 3.93 (3H, s); 3.90 (3H, s)

HRMS:calcd. for C$_{30}$H$_{26}$N$_4$O$_3$ (M$^+$):490.2005, found: 490.2024.

EXAMPLE 5

3-[1-(5-Aminomethyl-2-bromobenzyl)-indol-3-yl]-4-(1-methyl-indol-3-yl)-pyrrole-2,5-dione hydrochloride a) 3-[1-(2-Bromo-5-(methylisoindol-1,3-dion-2-yl)-benzyl)-indol-3yl]-4-(1-methyl-indol-3-yl)-furan-2,5-dione Sodium hydride (4.5 mg, 0.19 mmol) and 3-(indol-3-yl)-4-(1-methyl-indol-3-yl)-furan-2,5-dione (55 mg, 0.16 mmol) was stirred in dry dimethylformamide (1 mL) for 10 min. A solution of 2-(4-bromo-3-bromomethyl-benzyl)-isoindol-1,3-dione, in dry dimethylformamide (4 mL) was added and the resulting mixture stirred for 2 h. The reaction was quenched with 2 mL of 0.5 M HCl, the reaction mixture partioned between ethyl acetate and water, and the organic phase evaporated to yield the sub-title product.

b) 3-[1-(2-Bromo-5-(methylisoindol-1,3-dion-2-yl)-benzyl)-indol-3-yl]-4-(1-methyl-indol-3-yl)-pyrrole-2,5-dione The crude product from step a) was dissolved in dry dimethylformamide (5 mL), hexamethyldisilazan (0.2 mL) and methanol (0.02 mL) and the mixture stirred for 2 h. Additional portions of hexamethyldisilazane (0.4 mL) and methanol (0.04 mL) were added, and the mixture stirred for a further 6 days at room temperature. Evaporation gave the sub-title product.

c) The crude product from step b), ethanolic methylamine (2.9M, 1.5 mL) and tetrahydrofuran (1.5 mL) were combined and stirred overnight in a sealed flask. An additional 1.0 mL of the methylamine solution was added and the reaction mixture was stirred for another hour. Evaporation followed by chromatography (ethyl acetate/methanol/ammonium hydroxide:90/10/1) gave 65 mg of crude product. This was partitioned between ethyl acetate and sat. NaCl (aq). The organic phase was separated and thereafter azeotropically evaporated together with ethanol. Chromatography (methylene chloride/methanol/ammonium hydroxide:50/5/1) gave the title product as free amine. This was dissolved in ethanolic HCl (3.6 M, 30 ml) and evaporated, then redissolved and evaporated twice using ethanol, and once using methanol, to afford 42.0 mg of the title compound.

$^1$H-NMR (CD$_3$OC):δ7.82 (1H, s)(; 7.80 (1H, d, J=8.0 Hz); 7.76 (1H, s); 7.39 (1H, d, J=8.0 Hz); 7.37 (1H, d, J=8.0 Hz); 7.09 (1H, t, J=8.0 Hz); 7.07 (1H, t, J=8.0 Hz); 7.04 (1H, s); 6.96 (1H, d, J=8.0 Hz); 6.85 (1H, d, J=8.0 Hz); 6.71 (1H, t, J=8.0 Hz); 6.65 (1H, t, J=8.0 Hz); 5.58 (2H, s); 4.00 (2H, s); 3.90 (3H, s).

HRMS:calcd. for C$_{29}$H$_{24}$BrN$_4$O$_2$.Cl(M$^+$):538.1004, found:538.1030.

EXAMPLE 6

3-[1-(3-Aminomethyl-2,4-dimethoxy-benzyl)-indol-3-yl]-4-(1-methyl-indol-3-yl)-pyrrole-2,5-dione a) 3-[1-(2,4-Dimethoxy-3-(methylisoindol-1,3-dion-2-yl)-benzyl)-indol-3-yl]-4-(1-methyl-indol-3-yl)-furan-2,5-dione Sodium hydride (4.98 mg, 0.21 mmol, 55–60% oil dispersion) was added to 3-((indol-3-yl)-4-(1-methyl-indol-3-yl)-furan-2,5-dione (38 mg, 0.11 mmol) in dry dimethylformamide (1 mL). The mixture was kept at ambient temperature for 15 min, and then transferred with a syringe to a flask containing crude 2-(2,6-dimethoxy-3-bromomethyl-benzyl)-isoindol-1,3-dione. The resulting mixture was stirred for 15 min. Evaporation followed by chromatography (ethyl acetate/heptane) furnished 37 mg of the sub-title product.

$^1$H-NMR (CDCl$_3$):δ7.82–7.76 (2H, m): 7.78 (1H, s); 7.71–7.65 (2H, m); 7.69 (1H, s); 7.30 (sH, 2d, J=8.5 Hz); 7.12 (1H, t, J=7.5 Hz); 7.06 (1H, t, J=7.5 Hz); 7.02 (1H, d, J=8.0 Hz); 6.83 (1H, d, J=8.5 Hz); 6.78 (1H, t, J=7.5 Hz); 6.78 (1H, d, J=8.5 Hz); 6.71 (1H, t, J=7.5 Hz); 6.53 (1H, d, J=8.5 Hz); 5.31 (2H, s); 4.96 (2H, s); 3.86 (3H, s); 3.83 (3H, s); 3.71 (3H, s).

MS-FAB:m/z 651 [M$^+$]

b) The product of step a) was dispersed in ammonium hydroxide (5 mL) and dimethylformamide (5 mL) and heated at 100° C. for 2 h in a sealed flask. The reaction mixture was cooled and the dimethylformamide evaporated. The residue was dissolved in ethyl acetate and water, followed by addition of ammonium hydroxide and brine until a separation of the phases was obtained. The aqueous phase was extracted with ethyl acetate and the combined organic phases evaporated with ethanol. Chromatography (ethyl acetate/methanol/ammonium hydroxide:80/20/1 v/v) afforded 9 mg of the title product.

$^1$H-NMR (CDCl$_3$):δ7.72 (1H, s); 7.65 (1H, s); 7.26 (1H, d, J=8.0 Hz); 7.26 (1H, d, J=8.0 Hz); 7.07 (1H, t, J=7.5 Hz); 7.03 (1H, t, J=7.5 Hz); 6.98 (1H, d, J=8.0 Hz); 6.83 (1H, d, J=8.5 Hz); 6.79 (1H, d, J=8.5 Hz); 6.72 (1H, t, J=7.5 Hz); 6.65 (1H, t, J=7.5 Hz); 6.55 (1H, d, J=8.5 Hz); 5.29 (2H, s); 3.95 (2H, s); 3.84 (3H, s); 3.81 (3H, s); 3.71 (3H, s)

HRMS:calcd. for C$_{31}$H$_{28}$N$_4$O$_4$ (M$^+$):521.219, found:521.218.

EXAMPLE 7

3-[1-(2-N,N-Dimethylaminomethyl-benzyl)-indol-3-yl]-4-(methyl-indol-3-yl)-pyrrole-2,5-dione a) 3-[1-(2-Bromomethyl-benzyl)-indol-3-yl]-4-(1-methyl-indol-3-yl)-furan-2,5-dione A suspension of 3-(indol-3-yl)-4-(1-methyl-indol-3-yl)-furan-2,5-dione (1.0 g, 3 mmol) and sodium hydride (154 mg, 3.5 mmol, 55–60% dispersion in oil) in dimethylformamide (20 mL) was stirred and cooled to 0° C., under a stream of nitrogen. After 35 min the solution was transferred to a dropping funnel and added slowly, over 40 min, to a solution of 1,2-bis-bromomethyl-benzene (3.8 g, 14.5 mmol) in dimethylformamide (6 mL). The resulting solution was stirred for 1 h at room temperature under a stream of nitrogen. The reaction was quenched by adding NaHCO$_3$ (aq), and extracted with ethyl acetate. The organic phase was washed with several portions of water and dried (MgSO$_4$). Evaporation followed by chromatography on silica (ethyl acetate:heptane, 3:7) afforded 270 mg of the desired product.

$^1$H-NMR (CDCl$_3$):δ7.84 (1H, s), 7.65 (1H, s), 7.1–7.4 (8H, m), 6.7–6.9 (4H, m), 5.51 (2H, s,), 4.50 (2H, s), 3.88 (3H, s).MS-FAB$^+$:m/z524 and 526 [M$^+$]

b) To a solution of the product of step a) (322 mg, 0.6 mmol) in dimethylformamide (8 mL) was added N,N-dimethylamine (6 mL, 33% in ethanol, 33 mmol). After stirring for 15 min at room temperature the reaction was acidifyed with HCl. The solvent was partly evaporated, and the remaining solution (ca 10 mL) was transferred to a high-pressure flask. Aqueous ammonia (15 mL) was added and the mixture was heated to 140° C., with stirring for 2 h. An orange solid was precipitated upon cooling the flask in an ice bath. Recrystallisation from methanol/methylene chloride furnished 164 mg of the title compound as an orange solid.

$^1$H-NMR (CDCl$_3$):δ7.75 (1H, s), 7.64 (1H, s,), 7.30 (1H, s) 6.98–7.29 (8H, m), 6.68–6.88 (4H, m), 5.59 (2H, s), 3.87 (3H, s), 3.41 (2H, s), 2.21 (6H, s). MS-FAB:m/z 489 [MH$^+$]

EXAMPLE 8

3-[1-(2-Aminomethyl-benzyl)-indol-3-yl]-4-(1-methyl-indol-3-yl)-pyrrole-2,5-dione Following the same procedure as described in Example 7, 3-[1-(2-bromomethyl-benzyl)-indol-3-yl]-4-(1-methyl-indol-3-yl)-furan-2,5-dione (250 mg, 0.47 mmol) was treated with ammonium hydroxide (10 mL) at 100° C. for 2.5 h in a high-pressure flask. After cooling, the mixture was extracted with ethyl acetate, and the organic phase washed with water and evaporated. Chromatography (methylene chloride/ethanol:95:5) gave 14 mg of the title compound.

$^1$H-NMR (CDCl$_3$):δ3.85 (3H, s), 3.92 (2H, s), 5.28 (2H, s), 6.68–7.85 (14H, m).MS-FAB:m/z 461 [MH$^+$].

EXAMPLE 9

The following compounds were prepared by reacting the corresponding mesylates with an excess of ethanolic ammonia or dimethylamine at room temperature overnight. The mesylates were either isolated by a method analogous to Example 1 or prepared in situ as in Example 3.

A) 3-[1-(4-N,N-Dimethylaminomethyl-benzyl)-indol-3-yl]-4-(1-methyl-indol-3-yl)-pyrrole-2,5-dione $^1$H-NMR (CDCl$_3$):δ2.75 (3H, s); 3.85 (3H, s); 4.15 (2H, s); 5.35 (2H, s); 6.7–7.75 (14H, m); 7.7 (1H, s)

MS-FAB:m/z 489 [NH$^+$]

B) 3-[1-(3-N,N-Dimethylaminomethyl-benzyl)-indol-3-yl]-4-(1-methyl-indol-3-yl)-pyrrole-2,5-dione $^1$H-NMR (DMSO-d$_6$):δ2.1 (6H, s);3.9 (3H, s); 3.35 (2H, s); 5.5 (2H, s); 6.5–7.9 (14H, m)

C) 3-[1-(4-Aminomethylbenzyl)-5-methoxy-indol-3-yl]-4-(1-methyl-indol-3-yl)-pyrrole-2,5-dione $^1$H-NMR (acetone-d$_6$):δ3.06 (3H, s); 3.92 (3H, s); 4.22 (2H, s); 5.48 (2H, s); 6.3–7.95 (13H, m); 9.7 (1H, s)

MS-FAB:m/z 490 [M$^+$]

D) 3-[1-(3-Aminomethylbenzyl)-5-methoxy-indol-3-yl]-4-1-methyl-indol-3-yl)-pyrrole-2,5-dione $^1$H-NMR (CDCl$_3$):δ3.11 (3H, s); 3.79 (3H, s); 3.83 (2H, s); 5.27 (2H, s); 6.3–7.75 (13H, m)

MS-FAB: m/z 490 [M$^+$]

E) 3-[1-(3-Aminomethylbenzyl)-4-methoxy-indol-3-yl]-4-(1-methyl-indol-3-yl)-pyrrole-2,5-dione $^1$H-NMR (CDCl$_3$):δ3.50 (3H, s); 3.84 (3H, s); 3.79 (2H, s); 5.21 (2H, s); 6.37–7.85 (13H, m)

MS-FAB:m/z 490 [MH$^+$]

F) 3-[1-(4-Aminomethylbenzyl)-4-methoxy-indol-3-yl]-4-(1-methyl-indol-3-yl)-pyrrole-2,5-dione $^1$H-NMR (CD$_3$OD):δ3.51 (3H, s); 3.88 (3H, s); 4.11 (2H, s); 5.38 (2H, s); 6.43–7.94 (14H, m)

MS-FAB:m/z 490 [M$^+$]

EXAMPLE 10

3-[1-(4-Aminomethyl-3-(2-(trimethylsilyl)ethoxymethoxy)benzyl)-indol-3-yl]-4-[1-methyl-indol-3-yl]pyrrole-2,5-dione a) 3-[1-(4-Hydroxymethyl-3-(2-trimethylsilyl)ethoxymethoxy)benzyl)-indol-3-yl]-4-(1-methyl-indol-3-yl)-pyrrole-2,5-dione 3-(1-Methyl-indol-3-yl)-4-(indol-3-yl)-furan-2,5-dione (2.21 g, 0.61 mmol) and sodium hydrid (55–60% dispersion in oil, 0.031 g, 0.76 mmol) were dissolved in dry dimethylformamide and stirred for 20 minutes at ambient temperature before adding acetic acid 4-bromomethyl-2-(2-(trimethylsilyl)ethoxymethoxy)benzyl ester (0.25 g, 0.64 mmol). The reaction was allowed to proceed for 20 hours before adding ethyl acetate (20 mL), water (5 mL) and saturated aqueous ammonium chloride (5 mL). The phases were separated and the aqueous phase extracted with ethyl acetate (20 mL). The combined organic phases were washed with water (2×20 mL), and dried over Na$_2$SO$_4$. Removal of the solvent furnished crude 3-[1-(4-acetoxymethyl-3-(2-(trimethylsilyl)ethoxymethoxy)benzyl)-indol-3-yl]-4-(1-methyl-indol-3-yl)furan-2,5-dione which was dissolved in dimethylformamide (3 mL) and ammonium hydroxide (9 mL). Heating to 75° C. in a sealed tube for four hours gave, after extraction with ethyl acetate and chromatography (ethyl acetate/heptane:60/40), 98 mg of the sub-title compound as a red solid.

$^1$H-NMR (CDCl$_3$):δ0.01 (6H, s), 0.90–0.98 (2H, m), 3.70–3.78 (2H, m), 3.86 (3H, s), 4.66 (2H, d, J 6.5 Hz), 5.24 (2H, s), 6.62–6.77 (3H, m), 6.85 (1H, d, J 8.1 Hz), 6.98–7.13 (4H, m), 7.16–7.30 (3H, m), 7.69 (1H, s), 7.74 (1H, s).

b) The product of step a) (0.183 g, 0.30 mmol), 2,6-lutidine (0.145 g, 1.35 g) and methansulfonic anhydride were dissolved in dry methylene chloride (3 mL) and stirred at ambient temperature for five hours. Ammonia (5 mL, 5.5% in isopropanol) was added and the reaction stirred for two hours. Water (5 mL) was added and the product extracted with ethyl acetate (3×5 mL), dried over Na$_2$SO$_4$ and chromatographed (ethyl acetate/ethanol/ammonium hydroxide:90/10/2) to afford 74 mg of the title product as a red solid.

¹H-NMR (CDCl₃):δ0.00 (6H, s), 0.90–0.98 (2H, m), 3.71–3.78 (2H, m), 3.80 (2H, s), 3.85 (3H, s), 5.24 (2H, s), 5.30 (2H, s), 6.61 (1H, dd, J 1.5, 7.7 Hz), 6.65–6.77 (2H, m), 6.85 (1H, d, J 8.0 Hz), 6.97–7.06 (2H, m), 7.09 (1H, t, J 7.6 Hz), 7.15 (1H, d, J 7.6 Hz), 7.22 (1H, d, J 8.1 Hz), 7.27 (1H, d, J 8.1 Hz), 7.70 (1H, s), 7.73 (1H, s).

MS-FAB:m/z607 [M⁺].

EXAMPLE 11

3-[1-(4-Aminomethyl-3-hydroxybenzyl)-indol-3-yl]-4-[1-methyl-indol-3-yl]pyrrole-2,5-dione hydrochloride The product of Example 10 (0.068 g, 0.11 mmol) was dissolved in methylene chloride (0.5 ml). Water (0.1 mL) was added and the solution cooled on ice. Trifluoroacetic acid (1 mL) was added and the reaction allowed to proceed for 30 minutes. Extractive workup with ethyl acetate followed by chromatography (ethyl acetate/ethanol/ammonium hydroxide:90/10/2) yields 3-[1-(4-aminomethyl-3-hydroxybenzyl)-indol-3-yl]-4-[1-methyl-indol-3-yl]-pyrrole-2,5-dione (0.012 g,) as a red solid. Treatment with hydrochloric acid yields the title compound.

¹H-NMR (CDCl₃):δ3.84 (3H, s), 4.08 (2H, s), 5.36 (2H, s), 6.63 (2H, d, J 7.6 Hz), 6.70 (1H, d, J 7.6 Hz), 6.77–6.84 (2H, m), 6.90 (1H, d, J 8.2 Hz), 6.97 (1H, t, J 8.2 Hz), 7.05 (1H, t, J 7.6 Hz), 7.21–7.28 (2H, m), 7.34 (1H, d, J 7.6 Hz), 7.75 (1H, s), 7.76 (1H, s).

MS-FAB:m/z 476 [M⁺].

EXAMPLE 12

3-[1-(4-Aminomethyl-2-(2-(trimethylsilyl)ethoxymethoxy)benzyl)-indol-3-yl]-4-(1-methyl-indol-3-yl)-pyrrole-2,5-dione This compound was prepared from [2-(5-Azidomethyl-2-bromomethyl-phenoxymethoxy)ethyl]trimethylsilane in a manner analogous to Example 4.

¹H-NMR (CDCl₃):δ0.00 (6H, s), 0.94–1.02 (2H, m), 3.77–3.81 (2H, m), 3.83 (2H, s), 3.85 (3H, s), 5.30 (2H, s), 5.34 (2H, s), 6.66–6.89 (5H, m), 6.97–7.13 (4H, m), 7.24–7.29 (2H, m), 7.72 (1H, s), 7.74 (1H, s).

MS-FAB:m/z 606[M⁺].

EXAMPLE 13

3-[1-(4-Aminomethyl-2-hydroxybenzyl)-indol-3-yl]-4-(1-methyl-indol-3-yl)-pyrrole-2,5-dione hydrochloride This compound was prepared in a manner analogous to Example 11 starting from the product of Example 12.

¹H-NMR (CD₃OD):δ3.90 (3H, s), 4.02 (2H, s), 5.44 (2H, s), 6.63–6.67 (2H, m), 6.84 (2H, t, J 8.6 Hz), 6.90 (2H, t, J 7.3 Hz), 6.94–6.99 (2H, m), 7.07 (1H, t, J 7.3 Hz), 7.32 (1H, d, J 8.5 Hz), 7.37 (1H, d, J 7.9 Hz), 7.78 (1H, s), 7.82 (1H, s).

FD-MS:m/z 476 [M⁺].

EXAMPLE 14

3-[1-(3-aminomethylbenzyl)-indol-3-yl]-4-(1-methyl-5-methoxy-indol-3-yl)-pyrrole-2,5-dione hydrochloride a) 3-[1-(3-Methylisoindol-2,3-dion-2-yl)-benzyl)-indol-3-yl]-4-(1-methyl-5-methoxy-indol-3-yl)-furan-2,5-dione Sodium hydride (60% dispersion in oil, 50 mg, 1.5 mmol) and 3-(1-methyl-5-methoxy-indol-3-yl)-4-(indol-3-yl)-furan-2,5-dione (360 mg, 0.97 mmol) in 10 mL of dimethylformamide were stirred at room temperature for 15 min. A portion of 2-(3-bromomethyl-benzyl)-isoindol-1,3-dione (350 mg, 1.1 mmol) was added and the resulting mixture stirred at room temperature for 2 h. The reaction mixture was quenched with 1M hydrochloric acid and extracted with ethyl acetate. Evaporation and recrystallization from acetone gave 492 mg of the sub-title product.

¹H-NMR (CDCl₃):δ2.88 (3H, s); 3.84 (3H, s); 4.82 (2H, s); 5.26 (2H, s); 6.71 (1H, d); 6.82 (1H, t); 6.93 (1H, d); 7.05–7.32 (10H, m); 7.68–7.83 (4H, m).

b) 3-[1-(3-(Methylisoindol-2,3-dion-2-yl)-benzyl)-indol-3-yl]-4-(1-methyl-5-methoxy-indol-3-yl)-pyrrole-2,5-dione The product from step a) (492 mg, 0.79 mmol), 10 mL of dimethylformamide and ammonium acetate (630 mg 8.2 mmol) were stirred at 80° C. overnight. Addition of water gave a precipitate which was filtered and washed with water. This product was used without further purification.

¹H-NMR (CDCl₃):δ2.88 (3H, s); 3.89 (3H, s); 4.87 (2H, s); 5.30 (2H, s); 6.19 (1H,s); 6.52–7.88 (16H, m).

c) The product from step b), tetrahydrofuran (5 mL) and methylamine (2 mL, 7.6M in ethanol) were stirred at room temperature for 1 day. Additional methylamine (1 mL, as above) was added and the mixture stirred at room temperature for another day. The reaction mixture was evaporated and the crude product dissolved in ethyl acetate. The organic phase was washed with water, dried and evaporated. The resulting crude 3-[1-(3-aminomethyl-benzyl)-indol-3-yl]-4-(1-methyl-5-methoxy-indol-3-yl)-pyrrole-2,5-dione was chromatographed twice. First with methanol/ammonium acetate (97:3) and then with methylene chloride/methanol/ammonium hydroxide (98:2:1). The hydrochloride salt was made in a manner analogous to that of Example 1. Final purification of the salt was performed by filtration through a C₁₈-reversed phase cartridge (elution with methanol/water:20/80) furnishing 100 mg of the pure title compound.

¹H-NMR (CD₃OD):δ2.85 (3H, s); 3.88 (3H, s); 4.09 (2H, s); 5.43 (2H, s); 6.11 (1H, s); 6.68 (1H, d); 6.81 (1H, t); 7.08 (1H, t); 7.18–7.41 (7H, m); 7.68 (1H, s); 7.88 (1H, s).MS-FAB:m/z 491 [MH⁺].

EXAMPLE 15

The following compounds were prepared in a manner analogous to that of Example 14.

A) 3-[1-(3-Aminomethylbenzyl)-5-methoxy-indol-3-yl]-4-(1-methyl-5-methoxy-indol-3-yl)-pyrrole-2,5-dione ¹H-NMR (Acetone-d₆):δ2.9 (3H, s); 3.13 (3H, s); 3.91 (3H, s); 4.96 (2H, s); 5.47 (2H, s); 6.27 (1H, s); 6.4 (1H, s); 6.58 (1H, d); 6.62 (1H, d); 7.25–7.38 (4H, m); 7.47 (1H, d); 7.61 (1H, s); 7.84 (1H, s); 7.97 (1H, s). MS-FAB:m/z 521 [MH⁺].

B) 3-[1(3-Aminomethylbenzyl)-5-bromo-indol-3-yl]-4-(1-methyl-indol-3-yl)-pyrrole-2,5-dione hydrochloride ¹H-NMR (CD₃OD):δ3.93 (3H, s); 4.10 (2H, s); 5.46 (2H, s); 6.64–6.76 (2H, m); 6.99–7.45 (9H, m); 7.79 (1H, s); 7.84 (1H, s). MS-FAB:m/z 540 [MH⁺].

C) 3-[1-(3-Aminomethylbenzyl)-7-ethyl-indol-3-yl]-4-(1-methyl-indol-3-yl)-pyrrole-2,5-dione hydrochloride ¹H-NMR (CD₃OD):δ1.96 (3H, t); 2.81 (2H, q); 3.86 (3H, s); 4.09 (2H, s); 5.67 (2H, s); 6.60–7.42 (11H, m); 7.65 (1H, s); 7.82 (1H, s).

D) 3-[1-(3-Aminomethylbenzyl)-indol-3-yl)]-4-(7-bromo-1-methyl-indol-3yl)-pyrrole-2,5-dione hydrochloride $^1$H NMR (CD$_3$OD):δ7.84 (1H, s); 7.73 (1H); 7.39–7.32 (4H, m); 7.20 (1H, d, J=7.3 Hz); 7.12 (1H, bd); 7.03 (1H, t, J=7.8 Hz); 6.91 (1H, d, J=7.3 Hz); 6.83 (1H, d, J=8.5 Hz); 6.73 (1H, t, J=7.4 Hz); 6.45 (1H, t, J=7.7 Hz); 5.48 (2H, s); 4.26 (3H, s); 5.92 (2H, s).

EXAMPLE 16

3-[1-(1-Aminomethyl-pyridin-2-ylmethyl)-indol-3-yl]-4-(1-methyl-indol-3-yl)-pyrrole-2,5-dione hydrochloride a) 3-[1-(6-Chloromethyl-pyridin-2-ylmethyl)-indol-3-yl]-4-(1-methyl-indol-3yl)-furan-2,5-dione Sodium hydride (60% dispersion in oil, 42 mg, 1.8 mmol), 3-(1-methyl-indol-3-yl)-4-(indol-3yl)-furan-2,5-dione (236 mg, 0.7 mmol) and dimethylformamide (8 mL) were stirred at room temperature for 1 h. The reaction mixture was cooled with ice and 2,6-bis-chloromethyl-pyridine (520 mg, 3.0 mmol) was added in one portion. Stirring was continued at room temperature for 65 h. The solvent was evaporated and the residue partitioned between ethyl acetate and water. The organic phase was washed with water, dried with MgSO$_4$, filtered and evaporated. Chromatography (ethyl acetate/heptane:50/50) gave the title compound, which was not pure. Further purification by Kugelrohr distillation (oil pump, 150° C.) afforded 156 mg of the sub-title product.

$^1$H-NMR (dimethylformamide-d$_1$):δ8.30 (1H, s); 8.24 (1H, s); 8.02 (1H, t, J=7.6 Hz); 7.71–7.66 (3H, m); 7.32–7.22 (3H, m); 7.17 (1H, d, J=7.9 Hz); 7.04 (1H, d, J=7.8 Hz); 6.95 (1H, t, J=7.9 Hz); 6.88 (1H, t, J=7.6 Hz); 5.86 (2H, s); 4.98 (2H, s); 4.13 (3H, s).

b) 3-[1-(6-azidomethyl-pyridin-2-ylmethyl)-indol-3-yl]-4-(1-methyl-indol-3-yl)-furan-2,5-dione Sodium azide (80 mg, 1.22 mmol) was added to a solution of the product from step a) 156 mg, 0.32 mmol) in dimethylformamide (5 mL). The mixture was stirred at ambient temperature overnight, and then partitioned between ethyl acetate and water. The aqueous phase was separated and the organic phase washed with water. Evaporation gave crude sub-title product.

c) 3-[1-(6-Azidomethyl-pyridin-2-ylmethyl)-indol-3-yl]-4-(1-methyl-indol-3-yl)-pyrrole-2,5-dione The product from step b) was heated with ammonium hydroxide (5 mL) and dimethylformamide (5 mL) at 75° C. for 5 h in a sealed flask. The flask was cooled and the content partitioned between ethyl acetate and water. The organic phase was washed with ammonium hydroxide. Evaporation afforded 188 mg of the sub-title product, which was used without further purification.

$^1$H-NMR (CDCl$_3$):δ8.23 (1H, s); 7.76 (1H, s); 7.71 (1H, s); 7.56 (1H, t, J=7.6 Hz); 7.26 (1H, d, J=8.2 Hz); 7.20 (2H, d, J=8.0 Hz); 7.12 (1H, d, J=8.0 Hz); 7.07 (1H, t, J=8.1 Hz); 7.05 (1H, t, J=8.1 Hz); 6.84 (1H, d, J=8.1 Hz); 6.79 (1H, t, J=7.6 Hz); 6.66 (1H, d, J=7.8 Hz); 6.66 (1H, t, J=7.5 Hz); 5.45 (2H, s); 4.48 (2H, s); 3.83 (3H, s).

c) The product from step b) (188 mg, 0.38 mmol) was mixed with Lindlar catalyst (380 mg) in ethyl acetate (3 mL) and ethanol (3 mL), and then hydrogenated at atmospheric pressure and at ambient temperature for 45 hours. Filtration, evaporation and chromatography (ethyl acetate/methanol/ammonium hydroxide:80/20/2) afforded 42 mg of the free amine. This was dissolved in 1.5M ethanolic HCl. Evaporation afforded 47 mg of the title compound.

$^1$H-NMR (CDCl$_3$/CD$_3$OD:1/1):δ7.82 (1H, s); 7.76 (1H, s); 7.79 (1H,t, J=7.8 Hz); 7.39 (1H, d, J=8.1 Hz); 7.30 (1H, d, J=8.3 Hz); 7.24 (1H, d, J=8.3 Hz); 7.10 (1H, t, J=7.3 Hz); 7.05 (1H, t, J=7.1 Hz); 7.02 (1H, d, J=7.8 Hz); 6.96 (1H, d, J=8.0 Hz); 6.89 (1H, d, J=8.0 Hz); 6.75 (1H, t, J=7.3 Hz); 6.69 (1H, t, J=8.3 Hz); 5.54 (2H, s); 4.30 (2H, s); 3.88 (3H, s).

EXAMPLE 17

3-[1-(3-Aminomethyl-phenyl)-indol-3-yl]-4-(1-methyl-indol-3-yl)-pyrrole-2,5-dione a) 3-[1-(3-(N-t-Butoxycarbonyl-aminomethyl)-phenyl)-indol-3-yl]-4-(1-methyl-indol-3-yl)-furan-2,5-dione Oxalyl chloride(0.20 mL, 2.3 mmol) was added to an ice cold solution of 1-(3-N-t-butoxycarbonyl-aminomethyl)-phenyl)-indole (557 mg, 1.79 mmol) in 20 mL of dry methylene chloride and the resulting mixture stirred for 20 min. Evaporation gave crude (1-(3-(N-t-butoxycarbonyl-aminomethyl)phenyl)indole-3-glyoxylyl chloride, which was redissolved in 20 mL of dry methylene chloride. This solution was slowly added at room temperature, to a stirred solution of 1-methylindole-3-acetic acid (0.339 mg, 1.79 mmol), triethylamine (0.5 ml, 3.36 mmol) and 10 mL of dry methylene chloride, in the presence of molecular sieves (4 Å). Stirring was continued for 16 h at room temperature. Evaporation followed by chromatography (ethyl acetate/heptane:50/50) afforded 422 mg of the sub-title product.

$^1$H-NMR (CDCl$_3$):δ7.87 (1H, s); 7.73 (1H, s); 7.50–7.48 (2H, m); 7.44 (1H, d, J=8.6 Hz); 7.32–7.13 (6H, m); 6.96 (1H, t, J=7.7 Hz); 6.92–6.83 (2H, m); 4.96 (1H, s, broad); 4.36 (2H, d, J 5.5 Hz); 3.89 (3H, s); 1.47 (9H, s).

b) 3-[1-(3-(N-t-Butoxycarbonyl-aminomethyl)-phenyl)-indol-3-yl]-4-(1-methyl-indol-3-yl)-pyrrole-2,5-dione The product from step a) (264 mg, 0.48 mmol) ammonium hydroxide (20 mL) and dimethylformamide (20 mL) where heated to 120° C. for 3.5 hours in a sealed tube. The cooled solution was poured on ethyl acetate (50 mL) and water (100 mL). The aqeous phase was separated, washed twice with water and dried (MgSO$_4$). Evaporation followed by chromatography (ethyl acetate/heptane: 50/50) afforded 168.7 mg of the sub-title product.

$^1$H-NMR (CDCl$_3$): δ7.78 (1 H, s); 7.66 (1 H, s); 7.65 (1 H, s, broad); 7.47 (1 H, d, J=8.2 Hz); 7.42 (1 H, d, J=7.8 Hz); 7.33–7.23 (5 H, m); 7.15 (1 H, t, J=6.6 Hz); 7.13 (1 H, t, J=7.6 Hz); 6.91 (1 H, t, J=7.5 Hz); 6.87 (1 H, d, J=8.5 Hz); 6.79 (1 H, t, J=7.5 Hz); 4.95 (1 H, t, J=5.4 Hz); 4.35 (2 H, d J=6.1 Hz); 3.86 (3 H, s); 1.48 (9 H, s).

c) The product from step b) (66.0 mg, 0.12 mmol), tetrhydrofuran (5 mL) and 5 mL of 5 M HCl (aq) were heated at 50° C. for 45 min. The mixture was poured into ethyl acetate and dilute ammonium hydroxide. The organic phase was washed 3 times with dilute ammonium hydroxide and once with water, and then evaporated. Chromatography (ethyl acetate/methanol/ammonium hydroxide: 95/5/1) gave 54 mg of the title product.

$^1$H-NMR (CDCl$_3$): δ7.78 (1 H, s); 7.67 (1 H, s); 7.48 (1 H, d, J=8.3 Hz); 7.44 (1 H, t, J=7.6 Hz); 7.32–7.22 (4 H, m); 7.22 (1 H, s); 7.15 (1 H, t, J=7.1 Hz); 7.14 (1 H, t, J=7.1 Hz); 6.92 (1 H, t, J=7.5 Hz); 6.87 (1 H, d, J=8.1 Hz); 6.79 (1 H, t, J=8.1 Hz); 3.91 (2 H, s); 3.86 (3 H, s).

EXAMPLE 18

3-[1-(5-Aminomethyl-2-methyl-benzyl)-indol-3-yl]-4-(1-methyl-indol-3-yl)-pyrrole-2,5-dione hydrochloride The free amine of the title compound was prepared in a manner analogous to that of Example 17. The corresponding hydrochloride salt was obtained by dissolving the amine (48 mg. 0.09 mmol) in 3 mL of ethanolic 3.5 M HCl. The mixture was evaporated and the residue redissolved in methanol and evaporated. Drying in vacuo furnished 48 mg of the title compound.

$^1$H-NMR (CDCl$_3$): δ7.72 (1 H, s); 7.53 (1 H, s); 7.26–7.19 (3 H, m); 7.16 (2 H, s); 7.06 (1 H, t, J=7.4 Hz); 7.02 (1 H, t, J=7.4 Hz); 6.97 (1 H, d, J=8.1 Hz); 6,82 (1 H, d, J=7.8 Hz); 6.81 (1 H, s); 6.72 (1 H, t, J 7.7= Hz); 6.66 (1 H, t J=7.7 Hz); 5.27 (2 H, s); 3.82 (3 H, s); 3.73 (2 H, s); 2.24 (3 H, s).

EXAMPLE 19

3-[1-(4-((1-Pyridinium)methyl)benzyl)-indol-3-yl]-4-(1-methyl-indol-3-yl)-pyrrole-2,5-dione methanesulfonate salt 3-[1-(4-Hydroxymethylbenzyl)-indol-3-yl]-4-[1-methyl-indol-3-yl]pyrrole-2,5-dione, (0.65 g, 1.45 mmol) prepared in a manner analogous to that of Example 1a), and pyridine (0.33 ml, 4.23 mmol) were dissolved in dry methylene chloride (15 mL). To this solution methanesulfonic anhydride (0.31 g, 1.83 mmol), dissolved in 5 mL of dry methylene chloride, was added and the reaction was allowed to proceed overnight at room temperature. Water (20 mL) and another portion of methylene chloride (20 mL) was added whereupon a red precipitate was formed. The precipitate was dissolved in water and filtered through a C$_{18}$-reversed phase cartridge (elution with methanol/water: 20/80), to give 490 mg of the title compound.

$^1$N-NMR (DMSO-d$_6$); δ2.34 (3 H, s), 3.89 (3 H, s), 5.52 (2 H, s), 5.85 (2 H, s) 6.54 (1 H, t, J=7.5 Hz), 6.65 (1 H, d, J=8.0 Hz), 6.70 (1 H, t, J=7.5 Hz), 6.94–7.06 (3 H, m), 7.24 (2 H, d, J=8.4 Hz), 7.38 (1 H, d, J=8.2 Hz), 7.43 (1 H, d, J=8.2 Hz), 7.52 (1 H, d, J=8.2 Hz), 7.88 (1 H, s), 7.93 (1 H, s), 8.16–8.23 (2 H, m), 8.64 (1 H, tt, J=1.3, 7.8 Hz), 9.21–9.25 (2 H, m), 10.99 (1 H, br s).

EXAMPLE 20

3-[1-(5-Aminomethyl-thiophen-2-ylmethyl)-indol-3-yl]-4-(1-methyl-indol-3-yl)-pyrrole-2,5-dione a) 3-[1-(5-Hydroxymethyl-thiophen-2-ylmethyl)-indol-3-yl]-4-(1-methyl-indol-3-yl)-pyrrole-2,5-dione This compared was prepared in a manner analogous to Example 1a).Thus, the anion of 3-(indol-3-yl)-4-(1-methyl-indol-3-yl)-furan-2,5-dione was treated with acetic acid 5-brommomethyl-thiophen-2-ylmethyl ester. Subsequent treatment with ammonium hydroxide gave the sub-title compound.

$^1$H-NMR (CDCl$_3$): δ3.85 (3 H, s); 4.73 (2 H, d); 5.44 (2 H, s); 6.64–7.33 (10 H, m); 7.47 (1 H, s); 7.68 (1 H, s); 7.75 (1 H, s).

b) The product from step a) was treated in a manner analogous to Example 4b) and 4c) giving the title product as the free amine.

$^1$H-NMR (CDCl$_3$); δ3.84 (3 H, s); 3.96 (2 H, s); 5.42 (2 H, s); 6.63–7.34 (11 H, m); 7.69 (1 H, s); 7.74 (1 Hs, s).

EXAMPLE 21

3-[1-(3-Aminomethylbenzyl)-5-carboxymethyl-indol-3-yl]-4-(1-methyl-indol-3-yl)-pyrrole-2,5-dione a) 2-[3-(5-Carboxymethyl-indol-1-ylmethyl)-benzyl]-isoindol-1,3-dione This compound was prepared in a manner analogous to Example 14a) starting from 2-(3-bromomethyl-benzyl)-isoindol-1,3-dione and 5-carboxymethyl-indole.

$^1$H-NMR (CDCl$_3$); δ3.94 (3 H, s); 4.80 (2 H, s); 5.32 (2 H, s); 6.62–8.37 (13 H, m).

b) 3-[1-(3-(Methylisoindol-2,3-dion-2-yl)-benzyl)-5-carboxymehyl-indol-3-yl]-4-(1-methyl-indol-3-yl)-pyrrole-2,5-dione the product from step a) was treated in a manner analogous to Example 17a) giving crude 3-[1-(3-methylisoindol-2,3-dion-2-yl)-benzyl)-5-carboxymethyl-indol-3-yl]-4-(1-methyl-indol-3-yl)-furan-2,5-dione, which was treated with ammonium acetate following the procedure in Example 14b) to give the crude sub-title compound. Purification by chromatography (chloroform/ethanol: 98/2) gave the pure sub-title compound.

$^1$H-NMR (CDCl$_3$): δ3.72 (3 H, s); 3.87 (3 H, s); 4.83 (2 H, s); 5.31 (2 H, s); 6.67 (1 H, t); 6.76 (1 H, t); 6.86 (1 H, d); 7.07 (1 H, t); 7.19–7.86 (15 H, m).

c) The product from step b) was was treated with methylamine following the procedure in Example 14c). The crude free amine was subjected to chromatography (methylene chloride/methanol/ammonium hydroxide: 97:3:0.5) furnishing the pure title product.

$^1$H-NMR (CDCl$_3$): δ3.67 (3 H, s); 3.81 (3 H, s); 3.82 (2 H, s); 5.27 (2 H, s); 6.62 (1 H, t); 6.71 (1 H, d); 6.89 (1 H, d); 7.03 (1 H, t); 7.12 (1 H, s); 7.17–7.24 (5 H, m); 7.68–7.73 (4 H, m).

EXAMPLE 22

3-[1-(8-Aminomethyl-isoindolo[2,1-a]-indol-11-yl]-4-(1-methyl-indol-3-yl)-pyrrole-2,5-dione a) N-[4-bromo-3-(2,3-dihydro-indol-1-ylmethyl)-benzyl]-2,2,2-trifluoro-acetamide A mixture of 4-bromo-3-bromomethyl-benzonitrile (2.66 g, 9.7 mmol), indoline (1.14 mL, 10.2 mmol) and triethylamine (1.60 mL, 11.5 mmol) was heated at reflux for 18 h in dry tetrahydrofuran (50 mL). The flask was cooled and ether (100 mL) was added. Evaporation gave crude 4-bromo-3-(2,3-dihydro-indol-1-ylmethyl)-benzonitrile.

The crude 4-bromo-3-(2,3-dihydro-indol-1-ylmethyl)-benzonitrile (3.04 g) dissolved in dry tetrahydrofuran (50 mL) was dropped to an ice-cold slurry of lithium aluminium hydride 4.16 g, 0.11 mmol) in dry tetrahydrofuran (50 mL). The mixture was stirred for 1 h at ambient temperature, and then heated at reflux for another hour. The flask was cooled on ice, and the reaction mixture quenched with water (4.2 mL) followed by 15% NaOH(aq) (4.2 mL). Additional water (12.6 mL) was added and the mixture stirred at ambient temperature for 1 h. The white precipitate was filtered and washed with tetrahydrofuran. Evaporation afforded crude 4-bromo-3-(2,3-dihydro-indol-1-ylmethyl)-benzylamine (3.20 g) as a yellow oil. This was stirred together with ethyl trifluoroacetate (2.5 ml, 20.9 mmol) in dry methylene chloride (50 mL) for 17 h at room temperature. Evaporation followed by chromatography (ethyl acetate/heptane: 25/75) gave the sub-title compound.

¹H-NMR (CDCl₃): δ7.58 (1 H, d, J=8.0 Hz); 7.31 (1 H, s); 7.14–7.02 (3 H, m); 6.70 (1 H, t, J=7.2 Hz); 6.54 (1 H, bs); 6.38 (1 H, d, J=7.8 Hz); 4.46 (2 H, d, J=5.7 Hz); 4.29 (2 H, s); 3.44 (2 H, t, J=8.1 Hz); 3.05 (2 H, t, J=8.4 Hz).

b) N-(4-bromo-3-indol-1-ylmethyl-benzyl)-2,2,2-trifluoro-acetamide

The product from step a) (758 mg, 1.84 mmol) in methylene chloride (20 mL) was deoxygenated in vacuo, put under nitrogen atmosphere and then cooled on an ice bath, 2,3-Dichloro-5,6-dicyano-1,4-benzoquinone (423 mg, 1.86 mmol) was added in small portion during 10 min, and the mixture was first stirred on an ice bath for 30 min and then at ambient temperature for additional 60 min. Filtration through a plug of silica with ethyl acetate/heptane (50/50) followed by evaporation afforded the sub-title compound.

¹H-NMR (CDCl₃); δ7.68 (1 H, d, J=7.3 Hz); 7.60 (1 H, d, J=8.3 Hz); 7.22–7.11 (4 H, m); 7.07 (1 H, d, J=8.6 Hz); 6.61 (1 H, d, J=3.1 Hz); 6.46 (1 H, bs); 6.37 (1 H, s); 5.38 (2 H, s); 5.25 (2 H, d, J=6.0 Hz).

c) 2,2,2-Trifluoro-N-isoindolo[2,1-a]indol-8-ylmethyl-acetamide

The product from step b) (716 mg, 1.74 mmol) and potassium acetate (177 mg, 1.80 mmol) were dissolved in N,N-dimethylacetamide (17 mL). The solution was deoxygenated in vacuo and put under nitrogen atmosphere prior to addition of tetrakis(triphenylphosphine)palladium(0) (200 mg, 0.17 mmol). The resulting suspension was heated on an oil bath at 130° C. for 3 h. Addition of water (100 mL) gave a white precipitate which was filtered, washed with water and dried to give the sub-title compound ¹H-NMR (DMSO-d₆): δ10.11 (1 H, bs); 7.80 (1 H, d, J=7.4 Hz); 7.62 (1 H, d, J=7.4 Hz); 7.53 (1 H, s); 7.47 (1 H, d, J=8.4 Hz); 7.38 (1 H, d, J=7.7 Hz); 7.16 (1 H, t, J=7.6 Hz); 7.05 (1 H, t, J=7.6 Hz); 6.68 (1 H, s); 5.23 (2 H, s); 4.50(2 H, s).

d) 3-(8-N-Trifluoroacetyl-aminomethyl-isoindolo[2,1-a] indol-11-yl)-4-(1-methyl-indol-3-yl)-pyrrole-2,5-dione The product from step c) was transformed to 3-(8-N-trifluoroacetyl-aminomethyl-isoindolo[2,1-a]indol-11-yl)-4-(1-methyl-indol-3-yl)-furan-2,5-dione in a manner analogous to Example 17a). Subsequent reaction with hexamethyldisilazane following the procedure in Example 5b), gave the sub-title compound.

¹H-NMR (Acetone-d₆): δ9.75 (1 H, bs); 8.96 (1 H, bs); 8.09 (1 H, s); 7.46 (1 H, s); 7.45 (1 H, d, J=8.5 Hz); 7.41 (1 H, d, J=8.2 Hz); 7.36 (1 H, d, J=8.2 Hz); 7.24 (1 H, d, J=8.1 Hz); 7.19 (1 H, d, J=8.1 Hz); 7.14 (1 H, t, J=7.7 Hz); 6.93–6.89 (2 H, m); 6.55 (1 H, d, J=8.2 Hz); 6.48 (1 Hz, t, J=7.6 Hz); 5.20 (2 H, q, J=17.8 Hz); 4.53 (2 H, d, J=5.4 Hz); 3.89 (3 H, s).

e) The product from step d) (39 mg, 0.07 mmol) was dissolved in a mixture of acetone (5 mL) and ammonium hydroxide (5 mL). The resulting solution was stirred in the dark under nitrogen for 21 h. Evaporation followed by chromatography (ethyl acetate/methanol/ammonium hydroxide: 80/20/2) afforded a contaminated product. Another chromatography as above furnished the pure title product.

¹H-NMR (CDCl₃/CD₃OD): δ7.94 (1 H, s); 7.35–7.32 (3 H, m); 7.25 (1 H, d, J=8.4 Hz); 7.14 (1 H, t, J=7.8 Hz); 7.12 (1 H, d, J=7.8 Hz); 7.08 (1 H, d, J=8.4 Hz); 6.95 (1 H, t, J=7.5 Hz); 6.92 (1 H, t, J=7.5 Hz); 6.63 (1 H, d, J=8.1 Hz); 6.54 (1 H, t, J=7.4 Hz); 5.05 (2 H, s); 3.80 (2 H, s); 3.80 (3 H, s).

EXAMPLE 23

The metabolism of compounds of the present invention was examined in lung microsomes. Rat and human lung microsomes were prepared by standard techniques. Compounds were exposed to microsome preparations containing a final protein content of 1 mg/ml, 0.1 M KH₂PO₄ and 50 μM test compound. Samples were taken after 0, 15 and 45 min incubation periods and the level of metabolism of the compound was determined using HPLC.

What is claimed is:

1. A compound of formula (IA)

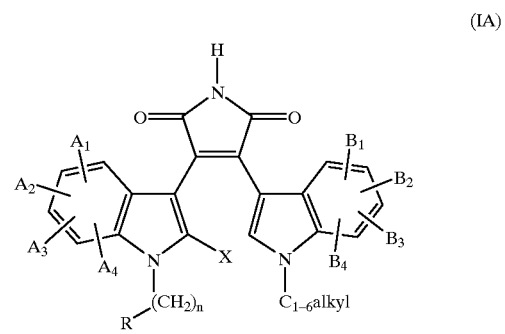

(IA)

wherein:
$A_1, A_2, A_3, A_4, B_1, B_2, B_3$ and $B_4$, which may be the same or different, are each hydrogen, $C_1$–$C_4$ alkyl, $C_1$–$C_4$ alkoxy, carboxy $C_1$–$C_4$ alkyl, or halogen, n is 0 or 1, R is a 5 or 6 membered aromatic carbocyclic or aromatic heterocyclic ring, the heterocyclic ring containing N or S, R is a substituted by $R_1$ and up to four of $R_2, R_3, R_4$, and $R_5$, wherein;

$R_1$ is aminomethyl, (N-($C_{1-4}$-alkyl)amino)methyl, (N,N-di($C_{1-4}$-alkyl)amino)methyl or pyridiniummethyl, and each of $R_3$, $R_4$ and $R_5$ independently, which may be the same or different, is hydrogen, hydroxy, $C_{1-6}$-alkoxy, $C_{1-6}$-alkyl, tri($C_{1-4}$-alkyl)silyl($C_{1-4}$-alkoxy)($C_{1-4}$-alkoxy), or halogen, and $R_2$ is hydrogen, hydroxy, $C_{1-6}$-alkoxy, $C_{1-6}$-alkyl, tri($C_{1-4}$-alkyl)silyl($C_{1-4}$-alkoxy)($C_{1-4}$-alkoxy), halogen or $R_2$ forms a ring together with the 2-carbon atom on the indole to which the —(CH₂)— group is attached when $R_2$ is in a position contigous to the bond connecting R to the —(CH₂)ₙ— group and n is 1; and X is hydrogen or is deleted when $R_2$ forms a ring together with the 2-carbon atom on the indole to which the —(CH₂)— group is attached where $R_2$ is in a position contigous to the bond connection R to the —(CH₂)ₙ— group and n is 1;

or a pharmaceutically acceptable salt thereof.

2. A compound according to claim 1, wherein $A_1, A_2, B_1$ and $B_2$ are hydrogen, and $A_3$ $A_4$, $B_3$ and $B_4$, which may be the same or different, are each hydrogen, $C_1$–$C_3$ alkyl, $C_1$–$C_3$ alkoxy, carboxy $C_1$–$C_3$ alkyl, or halogen;

$R_1$ is aminomethyl, (N-($C_{1-4}$-alkyl)amino)methyl or (N,N-di($C_{1-4}$alkyl)amino)methyl; and each of $R_3$, $R_4$ and $R_5$ independently, which may be the same or different, is hydrogen, hydroxy, $C_1$–$C_3$ alkyl, $C_1$–$C_6$ alkoxy or halogen; and $R_2$ is hydrogen, hydroxy, $C_{1-3}$-alkyl, $C_{1-6}$-alkoxy, halogen, or R₂ forms a ring together with the 2-carbon atom on the indole to which the —(CH₂)— group is attached when R₂ is in a position contiguous to the bond connecting R to the —(CH₂)ₙ— group and n is 1; and X is hydrogen or is deleted when R₂ forms a ring together with the 2-carbon atom on the indole to which the —(CH₂)— group is attached where R₂ is in a position contiguous to the bond connection R to the —(CH₂)ₙ— group and n is 1.

3. A compound according to claim 2, wherein
A₁, A₂, A₃, B₁, B₂, and B₃ are hydrogen, and A₄ and B₄, which may be the same or different, are each hydrogen, ethyl, methoxy, carboxymethyl, or halogen;
n is 1;
R₁ is aminomethyl; and
each of R₂, R₃, R₄ and R₅ independently, which may be the same or different, is hydrogen, hydroxy, methoxy, methyl or halogen; and
R₂ is hydrogen, hydroxy, methoxy, methyl, halogen, or
R₂ forms a ring together with the 2-carbon atom on the indole to which the —(CH₂)— group is attached when R₂ is in a position contiguous to the bond connecting R to the —(CH₂)ₙ— group and n is 1; and
X is hydrogen or is deleted when R₂ forms a ring together with the 2-carbon atom on the indole to which the —(CH₂)— group is attached where R₂ is in a position contiguous to the bond connection R to the —(CH₂)ₙ— group and n is 1.

4. A compound according to claim 1,
R₁ is aminomethyl,
R₁ is in a position meta to the —(CH₂)ₙ— group,
R is phenyl, pyridyl or thiophenyl and when R is thiophenyl the —(CH₂)ₙ— group is in the 2-position and the R₁ group is in the 5-position,
R₂ to R₅ are all hydrogen or one of R₂ to R₅ is bromine,
A₁, A₂, A₃, B₁, B₂, and B₃ are hydrogen, and
A₄ and B₄, which may be the same or different, are each hydrogen, methoxy, or carboxymethl;
or a pharmaceutically acceptable salt thereof.

5. The compound:
3-[1-(5-Aminomethyl-2-bromobenzyl)-indol-3-yl]-4-(1-methyl-indol-3-yl)-pyrrole-2,5-dione,
3-[1-(3-Aminomethylbenzyl)-indol-3-yl]-4-(1-methyl-indol-3-yl)-pyrrole-2,5-dione, 3-[1-(4-Aminomethylbenzyl)-indol-3-yl]-4-(1-methyl-indol-3-yl)-pyrrole-2,5-dione, 3-[1-(3-Aminomethylbenzyl)-5-methoxy-indol-3-yl]-4-(1-methyl-5-methoxy-indol-3-yl)-pyrrole-2,5-dione,
3-[1-(3-Aminomethylbenzyl)-7-ethyl-indol-3-yl]-4-(1-methyl-indol-3-yl)-pyrrole-2,5-dione,
3-[1-(6-Aminomethyl-pyridin-2-ylmethyl)-indol-3-yl]-4-(1-methyl-indol-3-yl)-pyrrole-2,5-dione,
3-[1-(5-Aminomethyl-thiophen-2-ylmethyl)-indol-3-yl]-4-(1-methyl-indol-3-yl)-pyrrole-2,5-dione,
3-[1-(3-Aminomethylbenzyl)-5-carboxymethyl-indol-3-yl]-4-(1-methyl-indol-3-yl)-pyrrole-2,5-dione,
or a pharmaceutically acceptable salts thereof.

6. The compound:
3-[1-(3-Aminomethylbenzyl)-indol-3-yl]-4-(1-methyl-indol-3-yl)-pyrrole-2,5-dione, 3-[1-(3-Aminomethylbenzyl)-5-methoxy-indol-3-yl]-4-(1-methyl-5-methoxy-indol-3-yl)-pyrrole-2,5-dione,
3-[1-(6-Aminomethyl-pyridin-2-ylmethyl)-indol-3-yl]-4-(1-methyl-indol-3-yl)-pyrrole-2,5-dione,
3-[1-(5-Aminomethyl-thiophen-2-ylmethyl)-indol-3-yl]-4-(1-methyl-indol-3-yl)-pyrrole-2,5-dione,
3-[1-(3-Aminomethylbenzyl)-5-carboxymethyl-indol-3-yl]-4-(1-methyl-indol-3-yl)- pyrrole-2,5-dione,
or a pharmaceutically acceptable salts thereof.

7. The compound:
3-[1-(3-Aminomethylbenzyl)-indol-3-yl]-4-(1-methyl-indol-3-yl)-pyrrole-2,5-dione,
or a pharmaceutically acceptable salts thereof.

8. The hydrochloride salt of compound according to claim 5.

9. A process for the preparation of a compound according to claim 1, comprising
a) production of a compound of formula (IA) in which R₁ is aminomethyl, by reduction of a corresponding compound in which R₁ is azidomethyl;
b) reaction of
(i) a compound of formula (III)

HNR₇R₈ (III)

in which R₇ and R₆, which may be the same or different, are each hydrogen or
C₁₋₄-alkyl, or
(ii) pyridine
with a corresponding compound of formula (IA) in which R₁ is a methyl group carrying a good leaving group;
c) production of a compound of formula (IA) in which R₁ is aminomethyl, by reaction of a compound of formula (IA) in which R₁ is a methyl group carrying a protected amino group, with a deprotecting agent;
d) production of a compound of formula (IA) in which R₁ is aminomethyl by reaction of a compound of formula (IV)

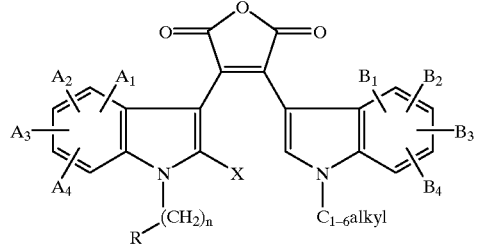

in which A₁–A₄, B₁–B₄, X, n and R are defined as in formula (IA), but in which R₁ is a methyl group carrying a protected amino group, with
(i) ammonia followed by treatment with a deprotecting agent;
(ii) ammonium acetate followed by treatment with a deprotecting agent; or
(iii) hexamethyldisilzane followed by treatment with a deprotecting agent;
e) production of a compound of formula (IA) in which R₁ is aminomethyl, by reaction of ammonia with a compound of formula (IV) in which A₁₋A₄, B₁–B₄, X, n and R are defined as in formula (IA), but in which R₁ is a methyl group carrying a halogen;
f) production of a compound of formula (IA) in which R₁ is a (N-(C₁₋₄-alkyl)amino)methyl or (N,N-di(C₁₋₄-alkyl)amino)methyl, by reaction of ammonia with a compound of formula (IV) in which $A_1$–$A_4$, $B_1$–$B_4$, X, n and R are defined as in formula (I), but in which $R_1$ is (N-($C_{1-4}$-alkyl)amino)methy or (N,N-di($C_{1-4}$-alkyl)amino)methyl;

g) production of a compound of formula (IA) in which one or more of $R_2$, $R_3$, and $R_4$ and $R_5$ (if present), are hydroxyl, by reaction of a compound of formula (IA) in which one or more of $R_2$, $R_3$, and $R_4$ and $R_5$ (if present), are oxygen carrying a protecting group, with a deprotecting agent; or h) converting a compound of formula (IA) to a pharmaceutically acceptable salt thereof, or vice versa.

10. A method for the treatment of an inflammatory or immunological disorder wherein a therapeutically effective amount of a compound according to claim 1 is administered to a mammal in the need of such treatment.

11. A pharmaceutical composition wherein the active ingredient is a compound according to claim 1.

12. The hydrochloride salt of a compound according to claim 6.

13. The hydrochloride salt of a compound according to claim 7.

14. A method for the treatment of an inflammatory or immunological disorder wherein a therapeutically effective amount of a compound according to claim 1 is administered to a mammal in the need of such treatment.

15. A method for the treatment of an inflammatory or immunological disorder wherein a therapeutically effective amount of a compound according to claim 2 is administered to a mammal in the need of such treatment.

16. A method for the treatment of an inflammatory or immunological disorder wherein a therapeutically effective amount of a compound according to claim 3 is administered to a mammal in the need of such treatment.

17. A method for the treatment of an inflammatory or immunological disorder wherein a therapeutically effective amount of a compound according to claim 4 is administered to a mammal in the need of such treatment.

18. A method for the treatment of an inflammatory or immunological disorder wherein a therapeutically effective amount of compound according to claim 5 is administered to a mammal in the need of such treatment.

19. A method for the treatment of an inflammatory or immunological disorder wherein a therapeutically effective amount of a compound according to claim 6 is administered to a mammal in the need of such treatment.

20. A method for the treatment of an inflammatory or immunological disorder wherein a therapeutically effective amount of a compound according to claim 7 is administered to a mammal in the need of such treatment.

21. A pharmaceutical composition wherein the active ingredient is a compound according to claim 1.

22. A pharmaceutical composition wherein the active ingredient is a compound according to claim 2.

23. A pharmaceutical composition wherein the active ingredient is a compound according to claim 3.

24. A pharmaceutical composition wherein the active ingredient is a compound according to claim 4.

25. A pharmaceutical composition wherein the active ingredient is a compound according to claim 5.

26. A pharmaceutical composition wherein the active ingredient is a compound according to claim 6.

27. A pharmaceutical composition wherein the active ingredient is a compound according to claim 7.

* * * * *